United States Patent [19]

Sugasawara et al.

[11] Patent Number: 5,556,770
[45] Date of Patent: Sep. 17, 1996

[54] METHOD OF PREPARING A COMPOSITION THAT ENHANCES

[75] Inventors: Renee J. Sugasawara, Rockville; Ruth B. Hill, Gaithersburg, both of Md.

[73] Assignee: Igen, Inc., Gaithersburg, Md.

[21] Appl. No.: 430,119

[22] Filed: Apr. 27, 1995

Related U.S. Application Data

[63] Continuation of Ser. No. 240,535, May 10, 1994, abandoned, which is a continuation of Ser. No. 101,341, Aug. 2, 1993, abandoned, which is a continuation of Ser. No. 683,086, Apr. 10, 1991, abandoned, which is a continuation of Ser. No. 822,826, Jan. 27, 1986, abandoned.

[51] Int. Cl.$^6$ .............................. C07K 1/14; C07K 1/16; C07K 1/22; C12P 21/00
[52] U.S. Cl. .................. 435/70.1; 435/240.1; 435/240.3; 435/244; 435/240.2; 435/240.25; 435/240.26; 435/240.27; 530/350; 530/413; 530/417
[58] Field of Search .............................. 435/240.1, 240.3, 435/244, 240.2, 240.25, 240.26, 240.27, 70.1; 530/350, 413, 417

[56] References Cited

PUBLICATIONS

"Multiple actions of interleukin 6 within a cytokine network" by Wong and Clark, 9 *Immunology Today* 137–139 (1988).
"A Macrophage–Derived Factor Required by Plasmacytomas for Survival and Proliferation in Vitro" by Nordan and Potter, 233 *Science* 566–569 (Aug. 1988).
"Identifiction of the Human 26kD Protein, Interferon B2 (IFN–B2), as a B Cell Hybridoma/Plasmacytoma Growth Factor Induced by Interleukin 1 and Tumor Necrosis Factor" by Van Damme, et al., 165 *J. Exp. Med.* 914–919 (Mar. 1987).
"Role of the Macrophage–Derived Hybridoma Growth Factor in the In Vitro and In Vivo Proliferation of Newly Formed B Cell Hybridomas" by Bazin and Lemieux, 139 *J. of Immunology* 78–787 (Aug. 1987).
"Purification and NH2–terminal amino acid sequence of T–cell derived lymphokine with growth factor activity for B–cell hybridomas" Van Snick et al., 83 *Vol. Natl. Acad. Sci.* 9679–9683 (Dec. 1986).
Altman, A. et al., Constitutive and Mitogen–In–duced Production of T. Cell Growth Factor by Stable T. Cell Hybridoma Lines, J. Immunol. 128, 1365 (1982).
Astaldi, G. C. B. et al., Human Endothelial Culture Supernatant (HECS): A Growth Factor For Hybridomas, J. Immunol. 125, 1411 (1980).
Cahoon, B. E. et al., Influence of Macrophage–Conditioned Media on Cloning Efficiency, Antibody Synthesis, and Growth Rate of Hybridomas, Hybridoma 3, 75 (1984).
Cerino, A. et al., Carboxyethyl–gamma–Aminobutyric Acid, a Polyamine Derivative Molecule with a Growth Effect on Hybridomas, J. Immunol. Met 77, 229 (1985).
Fagnani, R. and Braatz, J. A., Removal of Phytohemagglutinin from Conditioned Medium by Affinity Chromatography, J. Immunol. Met. 33, 313 (1980).

Fazekas De St. Groth, S. and Scheidegger, D., Production of Monoclohal Antibodies: Strategy and Tactics, J. Immunol. Met. 35, 1 (1980).
Howard, M., et al., Identification of a T Cell–Derived B Cell Growth Factor Distinct from Interleukin–2, J. Exp. med. 155, 914 (1982).
Issekutz, A. C. Removal of Gram–Negative Endotoxin from Solutions by Affinity Chromatography, J. Immunol. Met. 1, 275 (1983).
Kennett, R. H., Cell Fusion, Met. Enzymology 58, 345 (1979).
Lachman, L. B., et al., Preparation of a Lymphocyte–Activating Factor (LAF) from Continuous Murine Macrophage Cell Lines, Cell. Immunol. 34, 416 (1977).
Luben, R. A., Purification of a Lymphokine: Osteoclast Activating Factor from Human Tonsil Lyphocytes, Biochem. Biophys. Res. Comm. 84, 15 (1978).
Ma, M. et al., Enhanced Production of Mouse Hybridomas to Picomoles of Antigen Using EL–4 Conditioned Media with an *In Vitro* Immunization Protocol, In Vitro 20, 739 (1984).
Mizel, S. B. and Rosenstreich, D. L., Regulation of Lymphocyte–Activating Factor (LAF) Production and Secretion in P388D1. Cells: Identification of High Molecular Weight Precursors of LAF, J. Immunol 122, 2173 (1979).
Page, R. C. et al., The Macrophage as a Secretory Cell, International Review of Cytology 52, 119 (1978).
Payne, W. J. and Coggin, H. H., Jr. Mouse Monoclonal Antibody to Embryonic Antigen: Development, Cross–Reactivity with Rodent and Human Tumors, and Preliminary Polypeptide Characterization, J. Natl. Cancer Inst. 75, 527 (1985).
Pike, B. L., et al., Proliferation and Differentiation of Singel Hapten–Specific B Lymphocytes is Promoted by T–Cell Factor(s) Distinct From T–Cell Growth Factor, Proc. Natl. Acad. Sciences, USA, 79, 6350 (1982).
Pintus, C. et al., Endothelial Cell Growth Supplement: a Cell Cloning Factor that Promotes the Growth of Monoclonal Antibody Producing Hybridoma Cells, J. Immunol. Methods 61, 195 (1983).
Ralph, P. et al., Immunostimulators Induced Granulocyte/ Macrophage Colony–Stimulating Activity and Block Proliferation in a Monocyte Tumor Cell Line, J. Exp. 146, 611 (1977).

(List continued on next page.)

*Primary Examiner*—Donald E. Adams
*Attorney, Agent, or Firm*—John W. Ryan; Patrick J. Igoe

[57] ABSTRACT

The present invention provides a composition of matter useful for enhancing the viability of hybridomas in culture which comprises a partially purified, cell-free extract derived from a medium conditioned by mitogen-stimulated macrophages, the extract being substantially free of the macrophage stimulating mitogen which had been added to the medium, and having within it a component characterized by the ability to enhance the viability of hybridomas in culture, and by an apparent molecular weight in the range from about 35,000 to about 45,000. Also provided are methods of preparing the composition of matter, and methods for enhancing the viability of hybridomas in culture.

1 Claim, 1 Drawing Sheet

OTHER PUBLICATIONS

Reading, C. L., Theory and Methods for Immunization in Culture and Monoclonal Antibody Production, J. Immunol. Met. 53, 261 (1982).

Ratliff, T. L. et al., Production of Macrophage Activation Factor by a T–Cell Hybriodoma, Cell. Immunol. 68, 311 (1982).

Sugasawara, R. J. et al., Monoclonal Antibodies Against *Neisseria meningitidis* Lipopolysaccharide, Infect. Immun. 42, 863 (1983).

Sugasawara, R. J. et al., The Influence of Murine Macrophage–Conditioned Medium on Cloning Efficiency, Antibody Synthesis, and Growth Rate of Hybridomas, J. Immunol. Met. 79, 263 (1985).

Sugasawara, R. J. et al., Enhancement of Hybridoma Growth by Different Types of Macrophage–Conditioned Media, Hybridoma 4, 62 (1985).

Westerwoudt, R. J. et al., Improved Fusion Technique. I. Human Umbilical Cord Serum, a New and Potent Growth Promoter, Compared with Other B Cell and Hybridoma Activators, J. Immunol. Met. 62, 59 (1983).

Daenke, S. & Cox, K.O. Dependency of B Cells on the Presence of Adherent Cells, or Factors Derived from Them, for the Production of Autoantibodies in Vitro in the Absence of Cell Division, Scand. J. Immunol. 23, 567–573, (1986).

Walker, K. Z., et al., Potentiation of Hybridoma production by the use of mouse fibroblast conditioned media, Journal of Immunol. Methods, 88, 75–81, (1986).

Aarden, L. et al., A Growth Factor for B Cell Hybridomas Produced by Human Moncytes, Lymphokines, vol. 10, 175–185.

Issekutz, "Removal of Gram–negative endotoxin from solutions by affinity chromatography", J. Immun. Mehtods, vol. 61, 275–281, 1983.

Brodin, T. et al., Cloning of Human Hybridoma, Myeloma and Lymphoma Cell Lines using Enriched Human Monocytes as Feeder Layer, Elsevier Biomedical Press, (1982).

Namba, Y. et al., Immunocytology of Cultured IgM–Forming Cells Of Mouse, The Journal of Immunol., vol. 109, 1193 (1972).

Immunophysiology Ed. Oppenheim et al. Oxford Univ. Press 1990 Chapters 11 & 13.

Campbell, "Selection and Cloning", pp. 151–165, 1984 in *Monoclonal Antibody Technology*, Campbell, Elsevier, NY, NY.

Cahoon et al., "Influence of Machrophage–Conditioned Media on Cloning Efficiency, Antibody Syntheisis, and Growth Rate of Hybridomas", Hybridoma, vol. 3, p. 75, 1984.

Suegasawara et al (A), "The influence of murine macrophage–conditioned medium on cloning efficiency, antibody synthesis, and growth rate of hybridomas", J. Immun. Meth. vol. 79, 263–275 1985.

Sugasawara et al (B), "Enhancement of hybridoma growth by different types of macrophage–conditioned media", Hybridoma, vol. 4, p. 62, 1985.

Payne et al, Mouse Monoclonal Antibody to Embtyonic antigen: Development, cross–reactivity, with rodent and human tumors and preliminary polypeptide characterization, JNCI, vol. 75, 527–544, 1985.

Wood (A), "Mechanism of Action of Human B Cell–Activating Factor" Jm Immunology, vol. 123(5), 2400–2407, 1979.

Wood (B), "Purification and Properties of Human B cell–Activating Factor", J. Immunology, vol.123 (5) 2395–2399, 1979.

Reading, "Theory and Methods for Immunization in Culture and Monoclonal Antibody Production" J. Immunological Methods, vol. 53, 261–291, 1982.

Kull et al, "Necrosin: Purification and properties of a cytotoxin derived from murine macrophage–like cell line", PNAS, vol. 81, 7932 –7936.

Mizel et al, "Characterization of Lymphocyte–Activating Factor (LAF) produced by a macrophage Cell Line P388D", J. Immun. vol. 120, 1504–8, 1978.

METHOD OF PREPARING A COMPOSITION THAT ENHANCES

This is a file wrapper continuation of application Ser. No. 08/240,535, filed May 10, 1994, now abandoned, which was a file wrapper continuation of application Ser. No. 08/101,341, filed Aug. 2, 1993, now abandoned, which was a file wrapper continuation of application Ser. No. 07/683,086, filed Apr. 10, 1991, now abandoned, which was a file wrapper continuation of application Ser. No. 06/822,826, filed Jan. 27, 1986, now abandoned.

BACKGROUND OF THE INVENTION

Feeder layers comprised of murine thymocytes, fibroblasts, or macrophages have been commonly used to provide growth factors for hybridomas (6, 9). Additional growth factors are especially important during the aminopterin selection for hybridomas and during cloning to ensure monoclonality of the antibodies. However, feeder layers have several drawbacks: their preparation is labor intensive; they are a potential source of contamination; they may utilize nutrients intended for the hybridomas; and they may kill or overgrow the hybridomas they are intended to help. To obviate the later three problems, the hybridoma growth medium may be supplemented with human umbilical cord serum (24), carboxyethyl-gamma-aminobutyric acid (4), bovine hypothalamus extract (17), or the conditioned media of primary cultures of endothelial cells (2) or murine peritoneal macrophages (21).

The preparation of these conditioned media is also a time consuming and laborious task. A technician must obtain cells using sterile technique, count and then culture them at the appropriate density. After a predetermined time the conditioned medium is separated from the cells. One source of the cultured cells, such as macrophages, is the peritoneum of freshly sacrified mice. However, sacrificing and surgery can be distasteful. Additionally, obtaining human specimens is often extremely difficult or impossible, and therefore impractical for routine use.

The use of continuous cell lines, e.g. fibroblasts or macrophages, as a source of hybridoma growth factors has recently been examined. Fazekas De St. Groth and Scheidegger (6) attempted to use continuous macrophage cell lines as a source of feeder layers but found that the feeder layers often overgrew the hybridoma cultures.

It has been shown that the J774A.1, ATCC TIB 67, P388D1, ATCC TIB63 and RAW264.7, ATCC TIB 71 continuous macrophage cell lines produce a growth factor suitable for hybridoma growth and cloning (15, 22, 23). Mitogen stimulation is necessary for the BJ-1 macrophage cell line to produce the growth factor (3, 22). Conditioned medium prepared from J774A.1 cells without mitogen stimulation was evaluated for hybridoma viability enhancing properties during aminopterin selection but was found to be less effective than a J774A.1 conditioned medium which contained a stimulating mitogen (22, 23). J774A.1 cells which were stimulated for 72 hours with lipopolysaccharide (LPS), washed and then cultured in medium without the added lipopolysaccharide (second harvest) was also evaluated for hybridoma viability enhancing properties. The second harvest conditioned medium was also found to be less effective than the J774A.1 conditioned medium which contained a stimulating mitogen. The enhancement of hybridoma viability was highest in the J774A.1 medium which contained a stimulating mitogen, less in the medium collected from a second harvest in the absence of LPS, and lowest in the conditioned medium harvested from unstimulated J774A.1 cells (23). These data suggest that mitogen-stimulated macrophage cell conditioned media still containing the mitogen yields the desired result of hybridoma viability enhancement during aminoperin selection.

The use of different mitogens to stimulate macrophages to produce proteins such as colony stimulating factor has been well documented (13, 14, 18). Other cells such as B and T lymphocytes can also be stimulated by mitogens to produce lymphokines such as T-cell growth factor or interleukin-2 and osteoclast-activating factor (1, 5, 7, 10, 11). The conditioned medium of a phorbol myristic acetate stimulated thymoma cell line EL-4, serves as a replacement for lymphokines found in the conditioned medium of primary cultures of thymocytes which are necessary for in vitro immunization (12, 19).

The major drawback in using macrophage conditioned media as the source of macrophage-derived hybridoma growth factors (conditioned medium) is that it often contains mitogens which are used to stimulate the production of and/or increase the level of the growth factor in the medium, as well as numerous other enzymes, lymphokines, and cytotoxic factors. The presence of mitogens in the hybridoma growth medium can obscure in vitro immunological studies, e.g. it may stimulate hormone and interferon release or cyclic AMP synthesis (14). A macrophage conditioned medium containing hybridoma growth factors and which has reduced levels of endotoxins or mitogenic substances would be useful for growing hybridomas and minimizing the mitogenic/non-specific effects of various contaminants (e.g. endotoxins, plasminogen activator, interleukin-1, etc.).

SUMMARY OF THE INVENTION

The present invention provides a composition of matter useful for enhancing the viability of hybridomas in culture. This composition of matter comprises a partially purified, cell-free extract derived from a medium conditioned by mitogen-stimulated macrophages, the extract being substantially free of the macrophage stimulating mitogen which had been added to the medium. The extract has within it a component characterized by the ability to enhance the viability of hybridomas in culture and by an apparent molecular weight in the range from about 35,000 to about 45,000.

The invention also concerns a composition of matter useful for increasing the growth rate of hybridomas in culture or for increasing the amount of the monoclonal antibody produced by hybridomas, or both. This composition of matter comprises a partially purified, cell-free extract derived from a medium conditioned by mitogen-stimulated macrophages, the extract being substantially free of the macrophage stimulating mitogen which had been added to the medium. The extract has within it a component characterized by the ability to increase the growth rate of hybridomas in culture or to increase the amount of the monoclonal antibody produced by hybridomas, or both, and by an apparent molecular weight in the range from about 35,000 to about 45,000.

The invention further provides a substance characterized by the ability to enhance the viability of hybridomas in culture and by an apparent molecular weight in the range from about 35,000 to about 45,000. This substance is a component of a partially purified, cell-free extract derived from a medium conditioned by mitogen-stimulated macrophages, the extract being substantially free of the macrophage stimulating mitogen which had been added to the medium.

The present invention also provides a method for preparing a composition of matter useful for enhancing the growth of hybridomas in culture. This method comprises culturing suitable macrophage cells in an appropriate growth medium which contains a macrophage stimulating mitogen under conditions which allow the cells to secrete into the medium a substance characterized by the ability to enhance the growth of hybridomas in culture and by an apparent molecular weight in the range from about 35,000 to about 45,000, and recovering from the growth medium a partially purified, cell-free extract which is substantially free of the macrophage stimulating mitogen and which has within it the substance secreted by the macrophage cells which is characterized by its ability to enhance the viability of hybridomas in culture.

Also provided is a method for enhancing the viability of hybridomas in culture which comprises adding to the medium in which the cells are cultured an effective amount of a partially purified, cell-free extract derived from a medium conditioned by mitogen-stimulated macrophages, the extract being substantially free of the macrophage stimulating mitogen which had been added to the medium. The extract has within it a component characterized by the ability to enhance the viability of hybridomas in culture and by an apparent molecular weight in the range from about 35,000 to about 45,000.

Furthermore, a method is provided for increasing the growth rate of hybridomas in culture or for increasing the amount of the monoclonal antibody produced by hybridomas, or both, which comprises adding to the medium in which the hybridoma is cultured an effective amount of an partially purified, cell-free extract derived from a medium conditioned by mitogen-stimulated macrophages. The extract is substantially free of the macrophage stimulating mitogen which had been added to the growth medium and has within it a component characterized by the ability to increase the growth rate of hybridomas in culture or to increase the amount of the monoclonal antibody produced by hybridomas, or both, and by an apparent molecule weight in the range from about 35,000 to about 45,000.

DETAILED DESCRIPTION OF THE INVENTION

Figure 1:
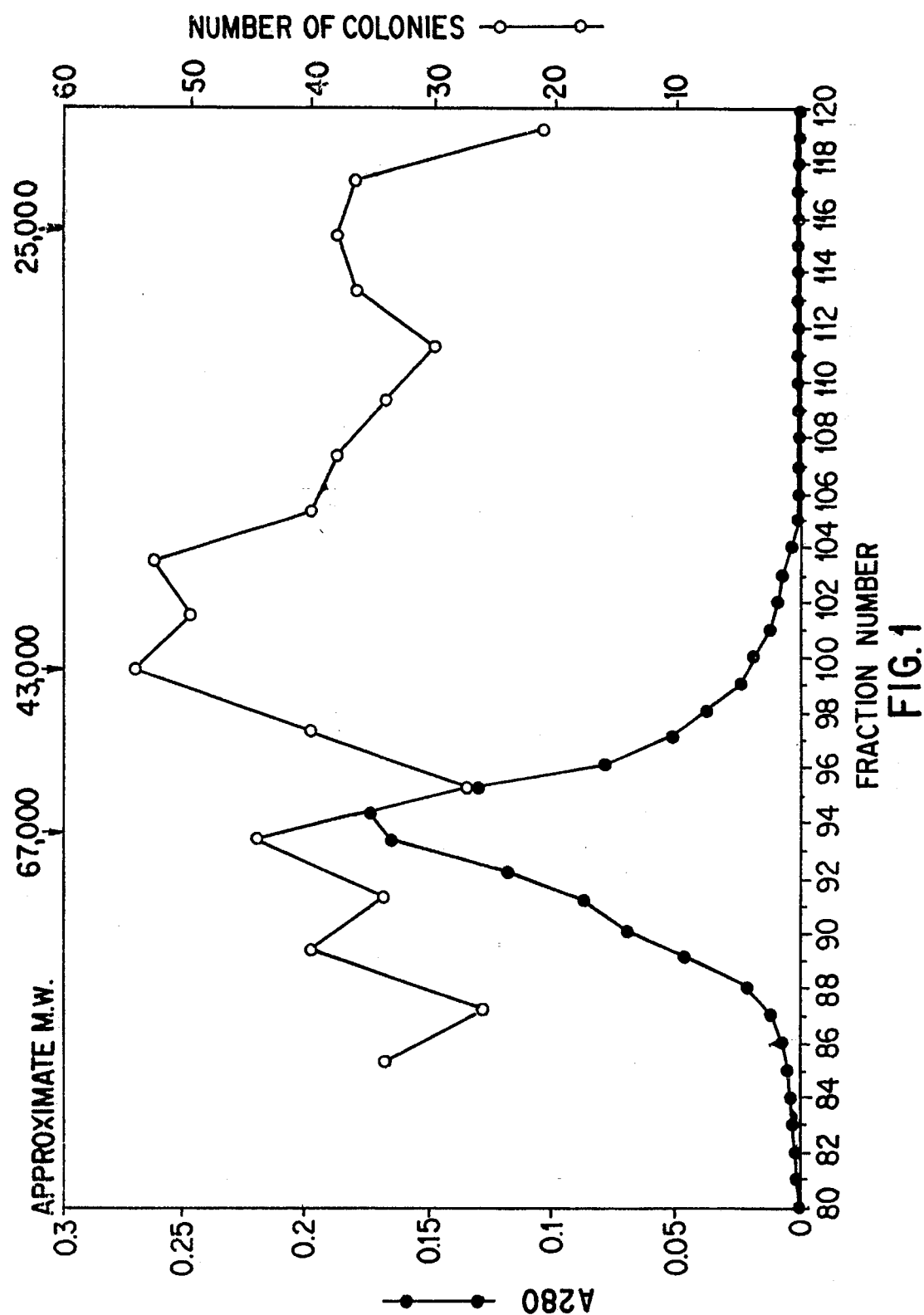
FIG. 1. Protein and hybridoma growth enhancing profile for the Sephacryl S-300 column.

The present invention provides a composition of matter useful for enhancing the viability of hybridomas in culture. This composition of matter comprises a partially purified, cell-free extract derived from a medium conditioned by mitogen-stimulated macrophages, the extract being substantially free of the macrophage stimulating mitogen which had been added to the medium. The extract has within it a component characterized by the ability to enhance the viability of hybridomas in culture and by an apparent molecular weight in the range from about 35,000 to about 45,000.

The mitogen-stimulated macrophages may be macrophages of murine origin, and may be in primary culture or derived from a continuous cell line. Suitable continuous cell lines, as used within this application, include the J774A.1, P388D.1, and RAW 264.7 cell lines. However, it is contemplated by the inventors that other cell lines known in the art may be used.

The medium conditioned by the mitogen-stimulated macrophages may be a medium suitable for culturing mammalian cells. As used within this application, a medium suitable for culturing mammalian cells is meant to include, but is not limited to, Iscove's Modified Dulbecco's Medium (IMDM), Roswell Park Memorial Institute formulation 1640 (RPMI-1640), HB101, HL-1, and Dulbecco's Modified Eagle Medium (DMEM).

In one embodiment of the invention, the composition of matter useful for enhancing the viability of hybridomas in culture is derived from material obtained by the gel filtration of extracellular material from the medium conditioned by mitogen-stimulated macrophages.

The supernatant derived upon the ammonium sulfate precipitation of the composition of matter useful for enhancing the viability of hybridomas in culture may also be used to enhance the viability of hybridomas in culture.

The invention also concerns a composition of matter useful for increasing the growth rate of hybridomas in culture or for increasing the amount of the monoclonal antibody produced by hybridomas, or both. This composition of matter comprises a partially purified, cell-free extract derived from a medium conditioned by mitogen-stimulated macrophages, the extract being substantially free of the macrophage stimulating mitogen which had been added to the medium. The extract has within it a component characterized by the ability to increase the growth rate of hybridomas in culture or to increase the amount of the monoclonal antibody produced by hybridomas, or both, and by an apparent molecule weight in the range of about 35,000 to about 45,000.

The mitogen-stimulated macrophages may also be macrophages of murine origin, and may be in primary culture or derived from a continuous cell line. The medium conditioned by the mitogen-stimulated macrophages may be any medium suitable for culturing mammalian cells.

In one embodiment of the invention, the composition of matter useful for increasing the growth rate of the hybridomas in culture or for increasing the amount of monoclonal antibody produced by hybridomas, or both, is derived from material obtained by the gel filtration of extracellular material from the medium conditioned by the mitogen-stimulated macrophages. The supernatant derived upon the ammonium sulfate precipitation of this composition of matter may also be used to enhance the viability of hybridomas in culture.

The invention further provides a substance characterized by the ability to enhance the viability of hybridomas in culture and by an apparent molecular weight in the range from about 35,000 to about 45,000. This substance is a component of a partially purified, cell-free extract derived from a medium conditioned by mitogen-stimulated macrophages, the extract being substantially free of the macrophage stimulating mitogen which had been added.

The present invention also provides a method for preparing a composition of matter useful for enhancing the growth of hybridomas in culture. This method comprises culturing suitable macrophage cells in an appropriate growth medium which contains a macrophage stimulating mitogen under conditions which allow the cell to secrete into the medium a substance characterized by the ability to enhance the growth of hybridomas in culture and by an apparent molecular weight in the range from about 35,000 to about 45,000, and recovering from the growth medium a partially purified, cell-free extract which is substantially free of the macrophage stimulating mitogen and which has within it the substance secreted by the macrophage cells which is characterized by the ability to enhance the viability of hybridomas in culture.

In a preferred embodiment of the invention, extracellular material is recovered from the mitogen-stimulated-macrophage-condition medium, the macrophage stimulating mitogen is removed from the recovered extracellular material by affinity chromatography, and a composition of matter which is substantially free of the macrophage stimulating mitogen and which is useful for enhancing the growth of hybridomas in culture is recovered.

The suitable macrophage cells used in this method may be of murine origin. Furthermore, the macrophage cell may be in primary culture or derived from a continuous cell line. The growth medium may be a medium suitable for culturing mammalian cells.

The macrophage stimulating mitogen may be an endotoxin. In a preferred embodiment of the invention, the endotoxin is E. Coli 055:B5 lipopolysaccharide. Additionally, the macrophage stimulating mitogen may be a lectin e.g. phytohemagglutinin, concanavalin A, and pokeweed mitogen, or it may be 12-0-tetradecanoylphorbal-13-acetate (TPA).

In another embodiment of the invention, the extracellular material recovered from the mitogen—stimulated—macrophage—conditioned medium is fractionated with ammonium sulfate, ethanol, polyethylene glycol, or sodium sulfate.

In a preferred embodiment of the invention, the affinity chromatography technique comprises removing the macrophage stimulating mitogen from the recovered extracellular material with the antibiotic polymyxin B.

The extracellular material recovered from the mitogen—stimulated—macrophage—conditioned medium may be fractionated by apparent molecular weight by gel filtration. Furthermore, a partially purified, cell free extract which is substantially free of the macrophage stimulating mitogen and which has within it a component characterized by the ability to enhance the viability of hybridomas in culture, and by an apparent molecular weight in the range from about 35,000 to about 45,000 may be obtained by dialyzing the extracellular material from the mitogen—stimulated—macrophage—conditioned medium.

Also provided is a method for enhancing the viability of hybridomas in culture which comprises adding to the medium in which the cells are cultured an effective amount of a partially purified, cell-free extract derived from a medium conditioned by mitogen-stimulated macrophages, the extract being substantially free of the macrophage stimulating mitogen which had been added to the medium. The extract has within it a component characterized by the ability to enhance the viability of hybridomas in culture and by an apparent molecular weight in the range from about 35,000 to about 45,000.

In a preferred embodiment of the invention the cell density is not greater than one cell per 0.2 ml. In another embodiment of the invention the serum concentration of the medium is less than 20%. Additionally, the viability of hybridomas in culture may be enhanced during hybridoma selection.

A method is also provided for increasing the growth rate of hybridomas in culture or for increasing the amount of the monoclonal antibody produced by hybridomas, or both, which comprises adding to the medium in which the hybridomas is cultured an effective amount of a partially purified, cell-free extract derived from a medium conditioned by mitogen-stimulated macrophages. The extract is substantially free of the macrophage stimulating mitogen which had been added to the growth medium and has within it a component characterized by the ability to increase the amount of the monoclonal antibody produced by the hybridomas, or both, and by an apparent molecular weight in the range from about 35,000 to about 45,000. In a preferred embodiment of the invention the serum concentration of the medium is less than about 20%.

MATERIALS AND METHODS

EXAMPLES

Macrophage Growth and Induction in Flasks

The J774A.1 macrophage cell line #TIB67, American Type Culture Collection, Rockville, Md. was cultured in a growth medium consisting of Iscove's Modified Dulbecco's Medium (IMDM, Hazleton, Inc., Denver, Pa.) containing 2% heat-inactivated fetal-calf serum, 100 µg/ml of kanamycin sulfate, 5 µg/ml of insulin, 5 µg/ml of transferrin, 18 µg/ml of cholesterol, and 72 µg/ml of phosphatidylcholine. The cells were scraped from the bottom of 150 $cm^2$ tissue culture flasks (#3150, Costar Inc., Cambridge, Mass.) and induced with 1 µg/ml of Escherichia coli strain 055:B5 lipopolysaccharide (LPS, Calbiochem Behring, San Diego, Calif.) for 72 hours at 105 cells per ml of growth medium in 175 $cm^2$ tissue culture flasks (#3028, Falcon Plastics, Oxnard, Calif.). J774A.1 macrophage conditioned medium (JMCM) was prepared by harvesting JMCM from the cultures and filtering the medium through a 0.2 micron pore size filter. The culture were maintained at 37° C. and 5% $CO_2$ in air.

Macrophage Induction on Microcarrier Beads

J774A.1 macrophages were seeded on microcarrier dextran beads (Pharmacia Fine Chemicals, Piscataway, N.J.) at about $1-10 \times 10^4$ cells/rag and allowed to grow at 37° C. and 5% $CO_2$ in air until approximately half-confluent. LPS was added to the growth media to yield a final concentration of 1 µg per ml. The JMCM was harvested as described above.

Macrophage Growth and Stimulation In Serum-Free Medium

The J774A.1 macrophages were grown in the growth media outlined above except that the 2% fetal-calf serum was replaced with 1 mg of bovine serum albumin per ml of growth medium. Growth and attachment to the plastic surface of flasks or to microcarrier beads is enhanced by the addition of attachment factors contained in serum such as fibronectin to the serum-free medium. Another medium which has been used is RPMI 1640, although other media could also be used.

Lipopolysaccharide Removal and Assay

A polymyxin-B Sepharose column was prepared according to Issekutz (8) to remove endotoxin from JMCM. Endotoxin levels were determined with a chromogenic Limulus amebocyte lysate assay as described by the manufacturer (M.A. Bioproducts, Walkersville, Md.).

The optical densities of the samples were determined with a Beckman DU-50 spectrophotometer. E. coli strain 055:B5 LPS was used as the standard for these assays.

Biological Activity Assay

Biological activity in the JMCM was assessed by cloning a hybridoma cell line designated 36F6, derived from a fusion of SP2/0 myeloma cells and lymphocytes from BALB/c mice immunized with *Escherichia coli* flagellar protein. The 36F6 hybridoma cell line produced IgG type monolclonal antibodies and was a stable cell line for antibody production and growth. The 36F6 cell line was cultured in 96-well tissue culture plates at a density of 1 cell/well in IMDM containing 15% heat-inactivated fetal-calf serum, 100 µg/ml of kanamycin sulfate, $5 \times 10^{-5}$ M 2-mercaptoethanol alone or with either 20% MCM from primary cultures MCM or 5%–20% JMCM.

The presence of the cloning factor was determined by macroscopically counting colonies after 14 days of growth at 37° C. and 5% $CO_2$ in air.

The ability of the conditioned medium and purified conditioned medium to enhance the growth of hybridomas selected with aminopterin was also assessed. Murine hybridomas, comprised of BALB/c splenocytes and SP2/0 myeloma cells were prepared with polyethylene-glycol (21). The hybridomas were selected in hypoxanthine, aminopterin, and thymidine (HAT) while in the presence of the various conditioned media. The number of colonies obtained was determined by macroscopic counts after ten days of growth.

Concentration of JMCM

J774A.1-conditioned medium was concentrated at 4° C. with Aquacide II (Calbiochem- Behring, San Diego, Calif.), carboxymethylcellulose flakes (M.W. 500,000), and a Spectra Por 1 dialysis bag with a 6,000 to 8,000 M.W. pore size. The hybridoma growth promoting activity after cloning was retained within the bag. Therefore the factor has a M.W. greater than 8,000.

Salt Fractionation

The JMCM was fractionated by addition of saturated ammonium sulfate until the desired concentration is achieved, usually 70%.

Molecular Weight Separation

Separation of the conditioned medium into fractions based on molecular weight was achieved by gel filtration on a Sephacryl S300 column (2.6×100 cm) at a flow rate of 10 ml/hour.

DISCUSSION

The following is an example of the preparation of a composition of the present invention and its uses.

J774A.1 conditioned medium was harvested after 3 days of LPS stimulation at 1 mg of LPS per liter of growth media. The ability of the conditioned medium to enhance hybridoma viability was evaluated and confirmed by a cloning assay. (See Table I below)

TABLE I

| Percentage of Conditioned Media | Avg. Colonies Per Plate | Standard Deviation |
| --- | --- | --- |
| Cloning Media alone | 8 | 1.7 |
| 10% control JMCM (in 10% FCS*) | 64 | 8.5 |

TABLE I-continued

| Percentage of Conditioned Media | Avg. Colonies Per Plate | Standard Deviation |
| --- | --- | --- |
| 10% JMCM (in 2% FCS) | 53 | 3.6 |
| 5% JMCM (in 2%) | 61 | 9.6 |

*Fetal Calf Serum

The active J774A.1 conditioned medium that enhanced hybridoma viability and contained 1 mg per liter of LPS was then run over a 10 ml polymyxin B-Sepharose 4B column at a 10 ml per hour flow rate to remove the LPS.

Fractions of the J774A.1 conditioned medium which ranged in LPS concentration from 48 to 120 pg per ml of conditioned medium were pooled. A portion of this substantially LPS-free material was assayed for the ability to enhance hybridoma growth after cloning. (See Table below)

TABLE II

| Percentage of Conditioned Media | Colonies Per Plate |
| --- | --- |
| Cloning Media Alone | 0 |
| 10% JMCM (in 2% FCS) containing 1 mg of LPS per liter | 60 |
| 10% JMCM (in 2% FCS) containing less than 120 ng LPS per liter | 103 |

The ability of this substantially LPS-free material to support the growth of hybridomas during the aminopterin selection was also tested. (See Table III)

TABLE III

| Percentage of Conditioned Media | Avg. Colonies Per Plate | Standard Deviation |
| --- | --- | --- |
| No additional MCM | 61.2 | 13.8 |
| 20% MCM from primary culture | 80.2 | 12.0 |
| 10% control JMCM (in 4% FCS) containing 1 mg of LPS per liter | 98.9 | 11.2 |
| 10% JMCM (in 2% FCS) containing 1 mg of LPS per liter | 106.1 | 14.3 |
| 10% JMCM (in 2% FCS) containing less than 120 ng LPS per liter | 134.8 | 16.3 |

The substantially LPS-free J774A.1 conditioned medium was concentrated and then chromatographed on a Sephacryl S-300 column. The hybridoma viability enhancing activity chromatographs in the molecular weight range of 35,000 to 45,000.

Hybridoma cells were seeded at one cell per well in the cloning media containing each of the fractions. (See Table IV)

TABLE IV

| Concentration of JMCM or Fraction No. | No. Colonies Per Plate |
| --- | --- |
| No Conditioned Medium Added | 0 |
| 10% JMCM sample before S-300 | 90 |
| Fraction 85 | 34 |
| Fraction 87 | 28 |
| Fraction 89 | 40 |
| Fraction 91 | 34 |
| Fraction 93 | 45 |
| Fraction 95 | 27 |
| Fraction 97 | 40 |

TABLE IV-continued

| Concentration of JMCM or Fraction No. | No. Colonies Per Plate |
| --- | --- |
| Fraction 99 | 55 |
| Fraction 101 | 50 |
| Fraction 103 | 53 |
| Fraction 105 | 40 |
| Fraction 107 | 38 |
| Fraction 109 | 34 |
| Fraction 111 | 30 |
| Fraction 113 | 37 |
| Fraction 115 | 38 |
| Fraction 117 | 37 |
| Fraction 119 | 21 |

The protein profile and the cloning results are shown in FIG. 1.

Another embodiment of the present invention is the generation of the J7744A.1 conditioned medium wherein the medium is a serum-free growth medium. The effect of fibronectin on production of the growth factor into serum-free medium is as follows. Fibronectin (1 mg per liter) was added to the medium containing the LPS and the J774A.1 cells. Control flasks which contained the cells, LPS and serum-free medium or 10% serum but no fibronectin were also maintained. The conditioned medium was harvested in three days.

TABLE V

| Percentage of Conditioned Media | Avg. Colonies Per Plate | Standard Deviation |
| --- | --- | --- |
| No MCM added | 10.7 | 1.2 |
| 20% MCM from primary culture | 90.3 | 10.7 |
| 10% control JMCM in 10% FCS | 99.7 | 4.7 |
| 10% JMCM in serum-free media with fibronectin | 93.7 | 13.9 |
| 10% JMCM in serum-free media | 37.7 | 12.3 |

REFERENCES

1. Altman, A. et al., Constitutive and Mitogen-Induced Production of T Cell Growth Factor by Stable T Cell Hybridoma Lines, J. Immunol. 128, 1365 (1982).

2. Astaldi, G. C. B. et al., Human Endothelial Culture Supernatant (HECS): A Growth Factor For Hybridomas, J. Immunol. 125, 1411 (1980).

3. Cahoon, B. E. et al., Influence of Macrophage-Conditioned Media on Cloning Efficiency, Antibody Synthesis, and Growth Rate of Hybridomas, Hybridoma 3, 75 (1984).

4. Cerino, A. et al., Carboxyethyl-gamma-Aminobutyric Acid, a Polyamine Derivative Molecule with a Growth Effect on Hybridomas, J. Immunol. Met. 77, 229 (1985).

5. Fagnani, R. and Braatz, J. A., Removal of Phytohemagglutinin from Conditioned Medium by Affinity Chromatography, J. Immunol. Met. 33, 313 (1980).

6. Fazekas De St. Groth, S. and Scheidegger, D., Production of Monoclonal Antibodies: Strategy and Tactics, J. Immunol. Met. 35, 1 (1980).

7. Howard, M., et al., Identification of a T Cell-Derived B Cell Growth Factor Distinct from Interleukin-2, J. Exp. Med. 155, 914 (1982).

8. Issekutz, A. C. Removal of Gram-Negative Endotoxin from Solutions by Affinity Chromatography, J. Immunol. Met. 61, 275 (1983).

9. Kennett, R. H., Cell Fusion, Met. Enzymology 58, 345 (1979).

10. Lachman, L. B., et al., Preparation of a Lymphocyte-Activating Factor (LAF) from Continuous Murine Macrophage Cell Lines, Cell. Immunol. 34, 416 (1977).

11. Luben, R. A., Purification of a Lymphokine: Osteoclast Activating Factor from Human Tonsil Lymphocytes, Biochem. Biophys. Res. Comm. 84, 15 (1978).

12. Ma, M. et al., Enhanced Production of Mouse Hybridomas to Picomoles of Antigen Using EL-4 Conditioned Media with an In Vitro Immunization Protocol, In Vitro 20, 739 (1984).

13. Mizel, S. B. and Rosenstreich, D. L., Regulation of Lymphocyte-Activating Factor (LAF) Production and Secretion in P388D1 Cells: Identification of High Molecular Weight Precursors of LAF, J. Immunol 122, 2173 (1979).

14. Page, R. C. et al., The Macrophage as a Secretory Cell, International Review of Cytology 52, 119 (1978).

15. Payne, W. J. and Coggin, J. H., Jr., Mouse Monoclonal Antibody to Embryonic Antigen: Development, Cross-Reactivity with Rodent and Human Tumors, and Preliminary Polypeptide Characterization, J. Natl. Cancer Inst. 75, 527 (1985).

16. Pike, B. L., et al., Proliferation and Differentiation of Single Hapten—Specific B Lymphocytes is Promoted by T-Cell Factor(s) Distinct From T-Cell Growth Factor, Proc. Natl. Acad. Sciences, USA, 79, 6350 (1982).

17. Pintus, C. et al., Endothelial Cell Growth Supplement: a Cell Cloning Factor that Promotes the Growth of Monoclonal Antibody Producing Hybridoma Cells, J. Immunol. Methods 61, 195 (1983).

18. Ralph, P. et al., Immunostimulators Induced Granulocyte/Macrophage Colony-Stimulating Activity and Block Proliferation in a Monocyte Tumor Cell Line, J. Exp. Med. 146, 611 (1977).

19. Reading, C. L., Theory and Methods for Immunization in Culture and Monoclonal Antibody Production, J. Immunol. Met. 53, 261 (1982).

20. Ratliff, T. L. et al., Production of Macrophage Activation Factor by a T-Cell Hybridoma, Cell. Immunol. 68, 311 (1982).

21. Sugasawara, R. J. et al., Monoclonal Antibodies Against *Neisseria meningitidis* Lipopolysaccharide, Infect. Immun. 42, 863 (1983).

22. Sugasawara, R. J. et al., The Influence of Murine Macrophage-Conditioned Medium on Cloning Efficiency, Antibody Synthesis, and Growth Rate of Hybridomas, J. Immunol. Met. 79, 263 (1985).

23. Sugasawara, R. J. et al., Enhancement of Hybridoma Growth by Different Types of Macrophage-Conditioned Media, Hybridoma 4, 62 (1985).

24. Westerwoudt, R. J. et al., Improved Fusion Technique. I. Human Umbilical Cord Serum, A New and Potent Growth Promoter, Compared with Other B Cell and Hybridoma Activators, J. Immunol. Met. 62, 59 (1983).

What is claimed is:

1. A method to prepare a composition which enhances hybridoma growth said method comprises:
    (a) culturing the J774A.1 macrophage cell line (ATCC No. TIB 67) in growth media containing an amount of LPS effective to stimulate the production of a factor which enhances hybridoma growth;
    (b) obtaining said growth media from step (a) free of cells and passing said growth media over a polymyxin B Sepharose column to remove said LPS;
    (c) recovering fractions from said polymyxin B Sepharose column from which said LPS has been removed;

(d) concentrating the fractions obtained in step (c) by enclosing said fractions in a dialysis bag having a 6000–8000 MW pore size and diaryzing against carboxymethyl cellulose flakes, to obtain a concentrate;

(e) applying said concentrate to a size-fractionating column; and recovering fractions from said size-fractionating column in the molecular weight range of 35–45 kD wherein the size fractionating column is a Sephacryl s300 column.

* * * * *